United States Patent [19]

Smith

[11] Patent Number: 4,839,164
[45] Date of Patent: Jun. 13, 1989

[54] TREHALOSE CONTAINING COSMETIC COMPOSITION AND METHOD OF USING IT

[75] Inventor: Walter P. Smith, Stamford, Conn.

[73] Assignee: Estee Lauder, Inc., New York, N.Y.

[21] Appl. No.: 17,781

[22] Filed: Feb. 24, 1987

[51] Int. Cl.$^4$ .................... A61K 7/027; A61K 7/06; A61K 7/40; A61K 7/48

[52] U.S. Cl. ...................................... 424/64; 424/59; 424/60; 424/63; 424/70; 514/847; 514/937; 514/938; 514/944

[58] Field of Search .................... 514/847; 424/59, 70, 424/64, 63

[56] References Cited

U.S. PATENT DOCUMENTS

| | | | |
|---|---|---|---|
| Re. 28,781 | 4/1976 | Konig et al. | 424/361 |
| 2,320,098 | 5/1943 | Quisling | 167/85 |
| 3,972,997 | 8/1976 | Nakashio et al. | 424/49 |
| 4,130,667 | 12/1978 | Smith | 424/361 |
| 4,146,649 | 3/1979 | Siegel et al. | 424/361 |
| 4,151,304 | 4/1979 | Evans | 424/361 |
| 4,305,961 | 12/1981 | Tsutsumi et al. | 424/361 |
| 4,364,837 | 12/1982 | Pader | 252/173 |

FOREIGN PATENT DOCUMENTS

| | | | |
|---|---|---|---|
| 0180559 | 5/1986 | European Pat. Off. | 514/847 |
| 6055306 | 5/1981 | Japan | 514/847 |
| 1188614 | 4/1970 | United Kingdom | 424/63 |

OTHER PUBLICATIONS

Kalopissis et al, Chem. Abs., 1976, vol. 85, p. 25285q.
Hagiwara, Chem. Abs., 1980, vol. 93, p. 210109p.
Marissal et al, Chem. Abs., 1982, vol. 97, p. 188327s.
Otsu et al, Chem. Abs. 1986, vol. 104, p. 192928u.
Ogawa et al., Chem. Abs., 5/25/87, vol. 106, p. 182467v.
G. Barnett, "Emollient Creams And Lotions", *Cosmetics, Science and Technology*, vol. 1, pp. 27–83 (M. Balsam et al. 2d ed. 1972).
F. J. Berger et al., "Hair Conditioners, Lacquers, Setting Lotions, and Rinses", *Cosmetics, Science and Technology*, vol. 2 pp. 345–353 (M. Balsam et al. ed 1972).
P. G. I. Lauffer, "Lipsticks", *Cosmetics, Science And Technology* vol. 1, pp. 365–381 (M. Balsam et al. 2d ed. 1972).
*Membrane Fluidity in Biology*, vol. 4, pp. 150–159, Academic Press, Inc., Orlando, Fla. (R. C. Aloia et al. ed. 1985).
Physiology of Membrane Fluidity, vol. I, pp. 1–4 & vol. II, pp. 54–56, CRC Press, Inc., Boca Baton, Fla. (M. Shinitzky ed. 1984).
H. Pottel et al., "Correlation Between The Order Parameter And The Steady-State Fluorescence Anisotropy Of 1,6-Diphenyl-1,3,5 Hexatriene And Evaluation Of Membrane Fluidity", *Biochimica et Biophysica Acta*, 730, 181–186 (1983).
D. H. Powers, "Shampoos", *Cosmetics, Science And Technology*, vol. 2, pp. 73–99 (M. Balsam et al. 2d ed. 1972).
Richardson et al., "Chemical Modification Of Trehalose. Part XIV. Some Tetra-and Hexa-deoxy-derivatives And Their Aminoanalogues", *Journal of Chemical Society*, Perkin vol. 1, I, No. pp. 1520–1523 (1973).
R. Seltzer, Chemical and Engineering News, p. 24, Jul. 15, 1985.
M. Shinitzky et al., "Fluidity Parameters Of Lipid Regions Determined By Fluorescence Polarization", *Biochimica et Biophysica Acta*, 515, pp. 367–394 (1978).
M. Shinitzky et al., "Lipid Fluidity At The Submacroscopic Lev Determination by Fluorescence Polarization", *Chemistry and Physics of Lipids*, 30, pp. 261–282 at 275 (1982).
S. J. Strianse, "Hand Creams And Lotions", *Cosmetics, Science A Technology*, vol. 1, pp. 179–219 (M. Balsam et al. 2d ed. 1972).
W. J. Van Blitterswijk, "Lipid Structural Order Parameters (Reciprocal Of Fluidity) In Biomembranes Derived From Steady-State Fluorescence Polarization Measurements", *Biochimica et Biophysica Acta*, 644, 323–332 (1981).
R. P. Van Hoeven et al., "Fluorescence Polarization Measurements On Normal And Tumour Cells And Their Corresponding Plasma Membranes", *Biochimica et Biophysica Acta*, 551, 44–54 (1979).

*Primary Examiner*—Dale R. Ore
*Attorney, Agent, or Firm*—Richard M. Barnes

[57] ABSTRACT

The present invention relates to a cosmetic composition and to a method of using that composition to enhance the penetration of topically applied ingredients into the cells of the skin. The composition preferably comprises:

(a) at least one cosmetic ingredient selected from the group consisting of retinyl palmitate at a concentration of about 0.01 to about 1% by weight, pantethine or a cosmetically acceptable ester of pantethine at a concentration of about 0.1 to about 2% by weight, superoxide dismutase at a concentration of about 0.001 to about 1% by weight, and epidermal growth factor at a concentration of about 0.001 to about 1% by weight;

(b) about 0.1 to about 20% by weight of trehalose; and (c) a cosmetically acceptable vehicle.

10 Claims, No Drawings

TREHALOSE CONTAINING COSMETIC COMPOSITION AND METHOD OF USING IT

FIELD OF THE INVENTION

The present invention relates to a cosmetic composition and to a method of using that composition to enhance the penetration of topically applied ingredients into the cells of the skin.

BACKGROUND OF THE INVENTION

As stratum corneum cells mature and approach the outer layers of the skin, they undergo many changes. For one thing, the cells become full of keratin protein, which flattens the cells and shuts off most metabolic processes. For another, the total lipid content of the cells decreases, while the quantity of cholesterol in the cells increases.

The foregoing changes in the cells and the exposure of the cells at the skin surface to dry air, result in the dehydration of the cell membranes. Consequently, the cell membranes become crystalline (less fluid) and collapse, resulting in the formation of a layer of skin highly resistant to penetration of water-soluble and lipid soluble materials into the skin. This process is aggravated by natural processes, such as less skin lipid being produced in older individuals.

A number of different saccharides and disaccharides (e.g., sucrose, mannitol and trehalose) or esters thereof have previously been used in cosmetic compositions for moisturizing the skin. While it has been recognized that such products have had a cosmetic moisturizing effect on the skin, there has been no recognition that a specific disaccharide, namely, trehalose enhances penetration of certain beneficial cosmetically therapeutical ingredients into the skin cells.

SUMMARY OF THE INVENTION

The present invention is directed to cosmetic compositions having enhanced penetration of specific cosmetic ingredients into the skin cells (including the skin cells of the scalp) and to a method of using that composition. The composition of the invention comprises:

(a) at least one ingredient selected from the group consisting of retinyl palmitate, preferably at a concentration of about 0.01 to about 1% by weight; pantethine or a cosmetically acceptable pantethine ester, preferably at a concentration of about 0.1 to about 5% by weight; superoxide dismutase, preferably at a concentration of about 0.001 to about 1% by weight; and epidermal growth factor, preferably at a concentration of about 0.001 to about 1% by weight;

(b) an amount of trehalose that is effective to enhance the penetration of said at least one ingredient into the skin, preferably at a concentration of about 0.1 to about 20% by weight; and (c) a cosmetically acceptable vehicle.

Unless otherwise listed, all percentages by weight stated herein are based on the total weight of the composition.

Trehalose is a disaccharide otherwise known as α-D-glucopyranosyl-α-D-glucopyranoside. Unlike other disaccharides or sugar analogs that have been used in moisturizers for the skin, I have found that trehalose surprisingly functions to increase substantially the penetration of certain therapeutically beneficial materials into the skin, thereby enhancing the therapeutic effects of the materials on the skin.

DETAILED DESCRIPTION OF THE INVENTION

The ingredients used in the composition of this invention should be suitable for cosmetic use and should be compatible when used together in a particular composition.

As used herein, the term superoxide dismutase shall include materials that have superoxide dismutase activity. Preferably, the superoxide dismutase activity of such materials should be at least about 3000 units per mg of protein. Commercially available materials having superoxide dismutase activity that may be used include a superoxide dismutase product having an activity of 3000 units per mg of protein marketed by Sigma Chemical Company, and a superoxide dismutase product marketed by Secol Inc.

Pantethine is available from Sigma Chemical Company, pantethine palmitate is available from Daiichi Pure Chemical Company and pantethine sulfonate is available from Centerchem Inc. Retinyl palmitate is available from Hoffman La Roche Inc., and epidermal growth factor is available from Sigma Chemical Company and Canada Packers Inc.

Particularly preferred concentrations of the ingredients used in the composition of the invention are:

(a) trehalose: about 0.5 to about 5% by weight;

(b) retinyl palmitate: about 0.05 to about 0.5% by weight; pantethine or pantethine ester; about 1 to about 2% by weight; superoxide dismutase; about 0.1 to about 1% by weight; and/or epidermal growth factor: about 0.1 to about 1% by weight.

The cosmetically acceptable vehicle used in our composition should not be irritating or otherwise harmful to the skin and, preferably, should impart a pleasant odor or be odorless. the vehicle may be selected and combined with other ingredients and the final composition may take a number of different froms, e.g., it may take the form of skin care products such as creams and gels, hair care products such as shampoos and conditions, lotions for application to the skin (including the scalp), and lipsticks.

Shampoo formulations of the present invention will generally contain, in addition to the essential components identified above, water, a cleaning agent (e.g., a surfactant and/or a detergent) and, optionally, one or more of a thickening agent, a fragrance and a preservative.

Hair conditioner formulations of the present invention will generally contain, in addition to the essential components identified above, water and, optionally one or more of an emulsifier system, at least one conditioning agent (which provides surface slip), a preservative, and, a fragrance.

Skin care gels of the present invention will generally contain, in addition to the essential components identified above, water, a thickening agent and, optionally, at least one of a fragrance and a preservative.

Lotions of the present invention will generally contain, in addition to the essential components identified above, water and, optionally, an emulsifier, a preservative, and a fragrance.

Skin care creams of the present invention will generally be oil in water emulsions comprising the essential components of the composition of the present invention identified above, and optionally, at least one of a fragrance, a preservative, and an emulsifier.

Other ingredients such as sunscreens, mink oil, humectants and emollients, and medicinal ingredients (e.g., antifungal agents, antibiotics, antiseptics, and keratolytic agents) may also be added to the compositions of the present invention.

Cleaning agents that may be used in the compositions of the present invention include, but are not limited to, sodium lauryl sulfate, ammonium lauryl sulfate, sodium lauryl sarcosinate, Triton ®-X-100 (Rohm and Haas Co.), and triethanolamine lauryl sulfate.

Thickening agents that may be used in the compositions of the present invention include, but are not limited to, hydroxypropyl methyl cellulose, carbopols (manufactured by B. F. Goodrich Co.), magnesium-aluminum silicates (e.g., Veegum ®, manufactured by R. T. Vanderbilt Company, Inc.) and lauramide diethanolamine.

Any fragrances compatible with the particular vehicle and other ingredients utilized may be used in the compositions of the present invention.

Preservatives that may be used in the compositions of the present invention include, but are not limited, to imidazolinyl urea (available as Germall ®115, manufactured by Sutton Laboratories, Inc.), phenoxyethanol, methyl paraben, propyl paraben, butyl paraben, and combinations of two or three of the aforementioned parabens.

Emulsifiers that may be used in the compositions of the present invention include, but are not limited to, cholesterol, lecithin (phosphatidyl choline), compositions consisting essentially of beeswax and borax (e.g., 1 to 10 parts by weight of beeswax and about 0.1 to 1.0 parts by weight of borax), and compositions consisting essentially of stearic acid and triethanolamine (e.g., 1 to 15 parts by weight of stearic acid and about 0.1 to 2.0 parts by weight of triethanolamine).

Conditioning agents that may be used in the compositions of the present invention include, but are not limited to, hydrolyzed animal protein, panthenol, Merquat ®500 (Merck & Co., Inc.), stearalkonium chloride, and Ucare ® Polymer JR (Union Carbide Corporation).

Emollients that may be used in the compositions of the present invention include, but are not limited to, mineral oil, lanolin, petrolatum and squalene.

Humectants that may be used in the compositions of the present invention include, but are not limited to, panthenol, sodium lactate, and sodium pyrollidonecarboxylic acid.

Sunscreens that may be used in the compositions of the present invention include any recognized and approved sunscreen at appropriate levels.

The frequency of application of the compositions of the present invention to the skin will depend on such factors as the condition of the skin, the age of the individual to whom the composition is to be applied and the vehicle used. Generally, the compositions of the present invention will be applied from one to several times per week (e.g., as a shampoo) up to several times per day (e.g., as a skin care gel).

The following non-limiting Examples illustrate various compositions of the present invention.

EXAMPLES

The following formulations are prepared by mixing together the ingredients listed below:

EXAMPLE 1

| parts weight | ingredient |
|---|---|
| 64.0 | water |
| 1.0 | glucogen |
| 2.0 | propylene glycol |
| 0.1 | adenosine |
| 5.0 | serum proteins |
| 2.0 | hyaluronic acid |
| 10.0 | Keltrol ® xanthan gum (1% solution) |
| 6.0 | Carbowax ® 400 USP PEG-8 |
| 0.3 | Germall ® 115 (imidazolidinyl urea) |
| 0.1 | methyl paraben |
| 5.0 | hydrolysed animal protein |
| 1.0 | Ajidew ® N-50 (sodium pyrollidyl carboxylic acid) |
| 3.0 | trehalose |
| 0.5 | epidermal growth factor |

EXAMPLE 2

In the formulation of Example 1, replace the 3.0 parts by weight of trehalose with b 3.3 parts by weight of trehalose and replace the 0.5 parts by weight of epidermal growth factor with 0.2 parts by weight of vitamin A palmitate or vitamin A acid to prepare a vitamin A formulation.

EXAMPLE 3

In the formulation of Example 1, replace the epidermal growth factor by 0.5 parts by weight of superoxide dismutase to prepare a superoxide dismutase formulation.

I claim:
1. A cosmetic composition comprising
   (a) at least one ingredient selected from the group consisting of retinyl palmitate, pantethine, a cosmetically acceptable pantethine ester, superoxide dismutase, and epidermal growth factor;
   (b) an amount of trehalose effective to enhance the penetration of said at least one ingredient into the skin; and
   (c) a cosmetically acceptable vehicle.
2. A cosmetic composition according to claim 1, said composition comprising
   (a) at least one ingredient selected from the group consisting of retinyl palmitate at a concentration of about 0.1 to about 1% by weight, pantethine or a cosmetically acceptable pantethine ester at a concentration of about 0.1 to about 5% by weight, superoxide dismutase at a concentration of about 0.001 to about 1% by weight, and epidermal growth factor at a concentration of about 0.001 to about 1% by weight;
   (b) about 0.1 to about 20% by weight of trehalose, and
   (c) a cosmetically acceptable vehicle.
3. The cosmetic composition of claim 2, wherein the concentration of trehalose is about 0.5 to about 5.0 percent by weight of the composition.
4. The cosmetic composition of claim 1, said composition taking the form of a cream, a shampoo, a hair conditioner, a skin care gel, a lotion, or a lipstick.
5. The cosmetic composition of claim 4, said composition taking the form of a shampoo, said shampoo additionally comprising water and a cleaning agent.
6. The cosmetic composition of claim 5, said composition also comprising a fragrance and a preservative.

7. The cosmetic composition of claim 5, said composition also comprising a thickening agent, a fragrance and preservative.

8. The cosmetic composition of claim 4, said composition taking the form of a hair conditioner, said hair conditioner additionally comprising water.

9. The cosmetic composition of claim 8, said composition also comprising an emulsifier, at least one conditioning agent and a preservative.

10. The cosmetic composition of claim 9, said composition also comprising a fragrance.

11. The cosmetic composition of claim 4, said composition taking the form of a skin care gel, said skin care gel additionally comprising water and a thickening agent.

12. The cosmetic composition of claim 11, said composition also comprising a fragrance and a preservative.

13. The cosmetic composition of claim 4, said composition taking the form of a lotion, said lotion additionally comprising water.

14. The cosmetic composition of claim 13, said composition also comprising a fragrance and a preservative.

15. The cosmetic composition of claim 4, said composition taking the form of a cream, said cream additionally comprising at least one oil and water, said cream being an oil in water emulsion.

16. The cosmetic composition of claim 15, said composition also comprising a fragrance, preservative, and an emulsifier.

17. A method of enhancing the penetration into the cells of the skin of a material selected from the group consisting of retinyl palmitate, panthethine, a cosmetically acceptable panthethine ester, superoxide dismutase, and epidermal growth factor comprising applying said material to the skin together with an amount of trehalose effective to enhance such penetration.

18. The method of claim 17, wherein said material is applied as part of a cream, a shampoo, a hair conditioner, a skin care gel, a lotion, or a lipstick.

19. A method of enhancing the penetration of a material selected from the group consisting of retinyl palmitate, panthethine, a cosmetically acceptable panthethine ester, superoxide dismutane, and epidermal growth factor to the skin comprising applying to the skin the composition of claim 2.

20. The method of claim 19, wherein the concentration of trehalose is about 0.5 to about 5.0 percent by weight of the composition.

* * * * *